United States Patent [19]

Bauer et al.

[11] 4,192,947
[45] Mar. 11, 1980

[54] PROCESS FOR THE PRODUCTION OF AMINOPHENYLAMINOBENZIMIDAZOLES

[75] Inventors: Wolfgang Bauer, Maintal; Joachim Ribka, Offenbach (Main)-Bürgel, both of Fed. Rep. of Germany

[73] Assignee: Cassella Aktiengesellschaft, Frankfurt am Main, Fed. Rep. of Germany

[21] Appl. No.: 941,462

[22] Filed: Sep. 12, 1978

[30] Foreign Application Priority Data

Sep. 19, 1977 [DE] Fed. Rep. of Germany ....... 2742093

[51] Int. Cl.² .......................................... C07D 235/18
[52] U.S. Cl. ............................... 548/334; 260/559 A; 260/558 A
[58] Field of Search ........................................ 548/334

[56] References Cited

U.S. PATENT DOCUMENTS

| 3,624,100 | 11/1971 | Frick et al. | 548/334 |
| 4,001,268 | 1/1977 | Kovar et al. | 548/334 |
| 4,109,093 | 8/1978 | Arsac et al. | 548/334 |

FOREIGN PATENT DOCUMENTS

| 950146 | 6/1974 | Canada | 548/334 |
| 2601041 | 7/1976 | Fed. Rep. of Germany | 548/334 |
| 309036 | 9/1971 | U.S.S.R. | 548/334 |

Primary Examiner—Natalie Trousof
Attorney, Agent, or Firm—Connolly and Hutz

[57] ABSTRACT

A process for the production of

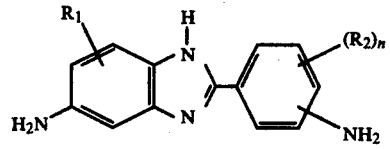

wherein $R_1$ and $R_2$ are the same or different and each is hydrogen, alkyl having 1–4 carbon atoms, alkoxy having 1–4 carbon atoms, chlorine or bromine, and n is 1 or 2 comprising reacting

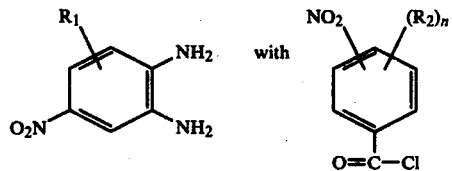

at $-10°$ C. to $100°$ C. at a pH of from 1–10 to form an anilide of the formula

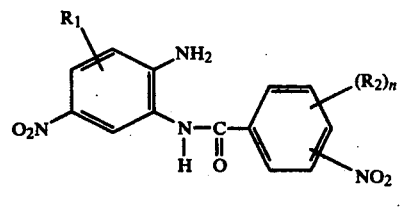

and cyclizing and reducing the anilide in an aqueous alkaline medium with a sulfide reducing agent.

9 Claims, No Drawings

PROCESS FOR THE PRODUCTION OF AMINOPHENYLAMINOBENZIMIDAZOLES

The present invention relates to a new process for the production of 2-(3'- or 4'-aminophenyl)-5(or 6)-aminobenzimidazoles of the general formula (I)

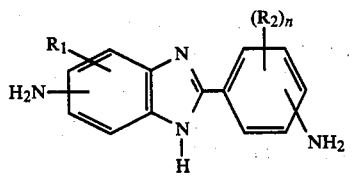

in which
R₁ and/or R₂=hydrogen
alkyl with 1 to 4 carbon atoms
alkoxy with 1 to 4 carbon atoms
chlorine or bromine
and
n signifies the numbers 1 or 2,
by the condensation shown in reaction diagram 1 of 4-nitro-1,2-diaminobenzenes of formula (II) with 3- or 4-nitrobenzoic acid chlorides of the formula (III) at pH values of 1 to 10 and temperatures of −10° C. to +100° C. to form 3- or 4-nitrobenzoic acid-2'-amino-5'-nitroanilides of the formula (IV) followed by their reduction with sulfide reducing agents and cyclisation by alkali treatment in an aqueous medium to form the heterocyclic diamines of the formula (I), it being possible for the reduction and the cyclisation to be carried out simultaneously in a single process stage or in separate process stages in any order of sequence in accordance with reaction diagram 1.

Reaction diagram 1

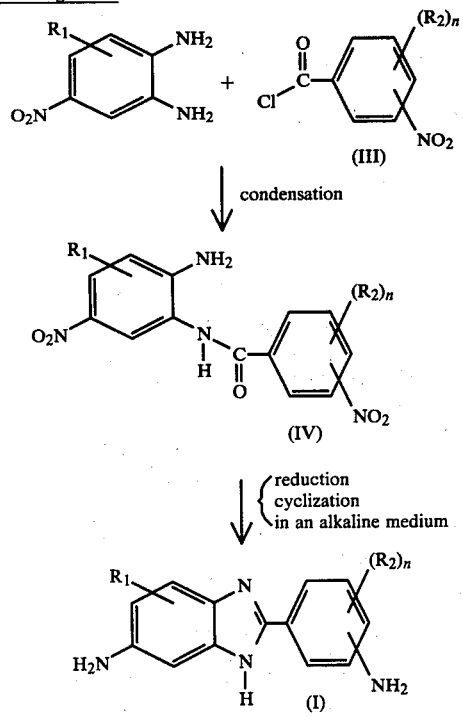

Heterocyclic diamines of formula (I) are accessible by means of various processes of preparation known from the literature. Thus it is known from
(a) O.Kym, Ber.dtsch. chem. Ges. 32, 2178 (1899);
(b) DRP No. 70 862 (26.7.1893); Frdl. III, 34 (1894);
(c) DRP No. 68 237 (8.3.1893); Frdl. III, 711 (1894);
(d) B. A. Porai-Koshits u. Ch. Frankovskii, Zhur, Obsc. Khim. 28, 928 (1958);
(e) V. k. Shchel'tsyn, A. Ya. Kaminskii, T. P. Shapirooskaya, J. L. Valsman, V. F. Adrianov and S. S. Gitis, Chemistry of Heterocyclic Compounds, USSR, 9, 103 (1973),
that aminophenylbenzimidazoles can be produced by reducing 3- or 4-nitrobenzoic acid-2',4'-dinitroanilides to 3- or 4-aminobenzoic acid-2',4'-diamino-anilides, which are converted by thermal or acid-catalysed cyclization into the heterocyclic diamines of formula (I).

The use of the trinitro compounds which act as strong oxidising agents as initial material in this process brings with it great risks.

Furthermore, the process described by O, Kym, Ber. dtsch. chem. Ges. 32, 2178 (1899), according to which the trinitro compounds are reduced in hydrochloric acid with tin (Hinsberg's method) to form 3- or 4-amino-benzoic acid-2',4'-diaminoanilides which in the presence of hydrochloric acid pass over by ring closure into the heterocyclic diamines (I), is disadvantageous as a result of the great pollution of effluents with metallic salts which today is no longer tolerable.

According to the information in the publications
(a) J. Pinnow and F. Wiskott, Ber. dtsch.chem.Ges. 32, 908 (1899);
(b) F. F. Stephens and J. D. Bower, J. chem. Soc. 1949, 2971;
(c) B. N. Feitelson, P. Mamalis, R. J. Monalim, V. Petrow, O. Stephenson and B. Sturgeon, J. chem. Soc. 1952, 2389;
(d) N. V. Subba Rao and C. V. Ratnam, Proc. Indian Acad. Sci. 49 A, 193 (1959)
it is possible for 2-(3'- or 4'-nitrophenyl)-5-(or6)-nitrobenzimidazoles of formula (IX) to be reduced to the heterocyclic diamines of formula (I).

This process, according to which heterocyclic diamines of formula (I) can be produced from the corresponding heterocyclic dinitro compounds is of little technical value because these dinitro compounds occur during the condensation of 4-nitro-1,2-diaminobenzenes (II) with 3- or 4-nitrobenzaldehydes as well as the 1-[3'- or 4'-nitrobenzyl]-2-[3'- or 4'-nitrophenyl]-5-(or 6)-nitrobenzimidazoles and are only accessible in a small yield.

Dinitrophenyl-benzimidazoles can also be produced by the nitration of 2-[3'- or 4'-nitrophenyl]-benzimidazoles or by the nitration of 2-phenylbenzimidazole.

These processes are also without any technical significance, because 2-[3'- or 4'-nitrophenyl]-benzimidazoles are also difficult to get at (cf. for example: R. Walter and Th. von Pulawski, J. prakt. Chem. 59, 263 (1899); J. Pinnow and F. Wiskott, Ber. dtsch. chem. Ges. 32, 898 (1899); O. Hinsberg and F. Funcke, Ber. dtsch. chem. Ges. 27, 2187 (1894); V. Sterba, J. Arient and J. Slosar, Collection Czech. Chem. Commun. 31, 1093 (1965), and the nitration of 2-phenylbenzimidazole leads to mixtures of 2-phenyl-5-(or 6)-nitrobenzimidazole, 2-[4'nitrophenyl]- and 2-[3'-nitrophenyl]-5-(or 6)-nitrobenzimidazole.

The dinitro compounds in this case occur in poor yields (cf. for example: D. G. Bapat and M. W. Shirsat, Indian J. Chem. 3, 81 (1965) and V. Sterba, J. Arient and J. Slosar, Collection Czech. Chem. Commun. 31, 1093 (1965)).

Heterocyclic diamines of formula (I) can be produced according to J. Preston, W. F. DeWinter and W. L. Hofferberth Jr., J. Heterocyclic Chem. 1969, 6 (1), 119, by the condensation of 1,2,4-triaminobenzene-di-hydrochlorides with 3- or 4-aminobenzoic acids in polyphosphoric acid at 190° to 220° C.

This process suffers from the disadvantage that the triaminobenzoles used as initial compounds are difficult to handle because they are compounds which are extremely sensitive to autoxidation and that the diaminobenzimidazoles of formula (I) in this process can only be isolated in a small yield.

According to a further process known from Canadian Pat. No. 950,146 for the production of 2-(4'-aminophenyl)-5-aminobenzimidazole (Ia) 4-nitro-1,2-diaminobenzene of formula (IIa) is condensed in a solvent mixture consisting of dimethyl acetamide, trethylamine and xylene with 4-nitrobenzoyl chloride (IIIa) to form 4-nitrobenzoic acid-2'-amino-5'-nitroanilide (IVa). After isolation, the compound of formula (IVa) is converted by thermolysis into 2-(4'-nitrophenyl)-5-nitrobenzimidazole (IXa), which is also isolated and then as a result of catalytic hydrogenation produces (Ia).

the reaction, the isolation of the condensation product of formula (IVa) and the regeneration of the solvents so as to keep effluents and exhaust air pure, for which purpose considerable additional apparatus is required and this process is made more expensive still.

Surprisingly, it has now been found that the cyclization of the anilides of formula IV can be carried out not only, as described exclusively in the literature, thermally or with acid catalysis, but in an unforeseeably smooth reaction in an alkaline medium. This permits of the execution of the new reaction sequence of the process of the invention in accordance with the reaction diagram 1 for the production of 2-[3'- or 4'-aminophenyl]-5(or 6)-aminobenzimidazoles (I), which does not show the disadvantages from which the processes mentioned above and known from the literature suffer.

The trinitro compounds which act as strong oxidising agents in the processes known from the literature are avoided in the process of the present invention. Furthermore, both the intermediate products of formula (IV) and also the heterocyclic diamines of the general formula (I) are obtained according to the process of the invention in a very good quality and in excellent yields which are considerably improved as compared with known processes.

A special technical advance of the process of the present invention as compared with the previously known processes is not only the high yield and the very Reaction diagram 2

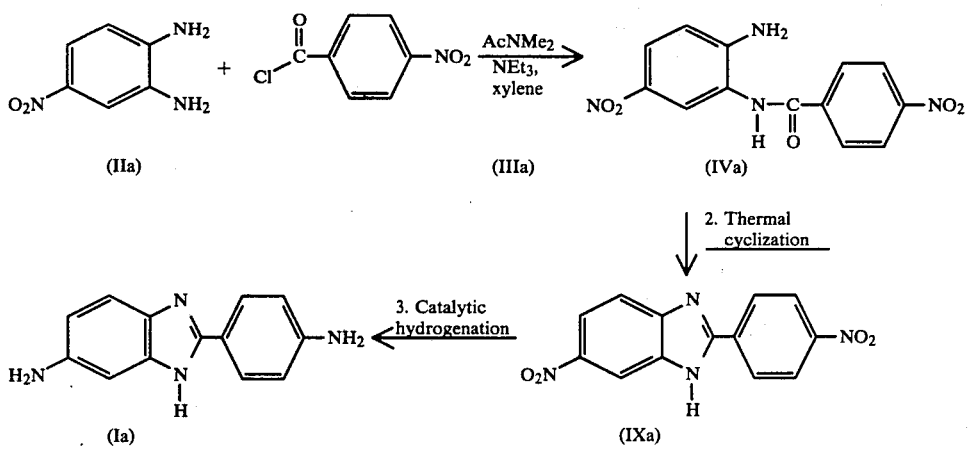

The process known from the sketch in reaction diagram 2 has the disadvantage that the heterocyclic diamine of formula (Ia) is produced in separate working stages, which are bound up with laborintensive isolation of intermediates (IVa) and (IXa), so that the process is made considerably more expensive as a result of long reaction times, losses of yield occurring during the intermediate isolation of products (IVa) and (IXa) and by the use of a larger amount of apparatus.

Furthermore, the process according to reaction diagram 2 brings with it difficulties in execution and processing with regard to the environment, because during the production of the condensation product of formula (IVa) both dimethyl acetamide and also triethylamine are used as solvents and the permissible MAK values of only 10 ppm for dimethylacetamide and 25 ppm for triethylamine must not be exceeded. As a result of this, special measures must be taken during the execution of good quality of the end products, but also because on account of the fact that because of the cyclization being carried out in an alkaline medium it can be carried out as a simple single-vessel process, that is to say without intermediate stages occurring in the form of intermediate isolation and purification, and that factory effluents occur which are free from heavy metal salts, and whose biological and chemical oxygen demand is low.

A further special economic advantage of the process of the present invention consists in the fact that as solvent in the reduction and cyclization stages it is possible to use water alone and, therefore, there is no regeneration of organic solvents and measures for maintaining the permissible MAK values. A further advantage in the use of sulfide reducing agents, especially sulfhydrate liquor as reducing agent, is to be found in the simple solution of effluent and exhaust air problems. As a result of the joint processing of the effluents and waste gases from the production of the nitrobenzoic acid chlorides III and from the reducing and cyclization stages an effluent is obtained which is very favorable from the ecological point of view and which contains no lowvalency sulfur compounds and whose biological and chemical oxygen demand is low.

The process of the present invention is carried out by first of all converting a 3- or 4-nitrobenzoic acid of the general formula VI with excess thionyl chloride or other acid-halogenating compounds, such as phosgene, phosphorus trichloride, phosphorus pentachloride, phosphorus oxychloride in a known manner (cf. Houben-Weyl, Methoden der Organischen Chemie, 4th edition, volume VIII, page 467 (1952); DRP No. 1,026,750) into the corresponding 3- or 4-nitrobenzoic acid chlorides of the general formula (III):

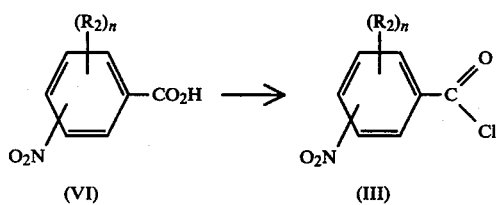

This reaction is generally carried out in the presence of small quantities of an organic nitrogen compound as catalyst, preferably dimethylformamide or pyridine, and at a rising temperature, preferably from 20° to 100° C. The reaction of the 3- or 4-nitrobenzoic acid (VI) to form the corresponding 3- or 4-nitrobenzoic acid chloride(III) is preferably carried out without a solvent, but it can also be carried out in inert organic solvents, for example methylene chloride, chloroform, carbon tetrachloride, dichlorethane, trichlorethane, n-hexane, cyclohexane, toluene, xylene, monochlorobenzene, o-dichlorobenzene.

The melt or solution so obtained of the 3- or 4-nitrobenzoic acid chloride (III) is—preferably without further purification—made to react with an aqueous suspension of a 4-nitro-1,2-diaminobenzene of the general formula (II), when 3- or 4-nitrobenzoic acid-2'-amino-5'-nitroanilides of formula (IV) are obtained.

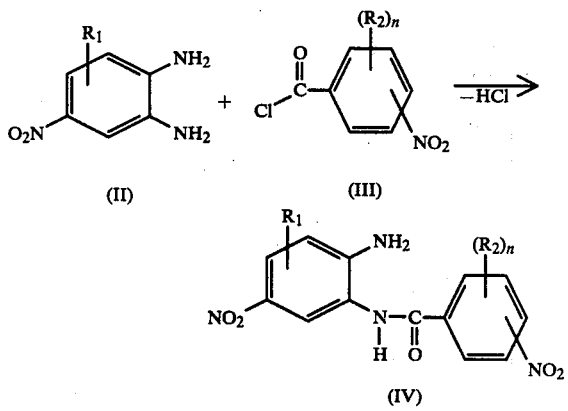

The condensation reaction is normally carried out at pH values between 1 and 10, preferably 1 and 5, and at temperatures of −10° to +100° C., preferably 0° to 50° C.

In order to maintain the optimum pH values of 1 to 10, preferably 1 to 5, in the condensation reaction, it is possible before or during the reaction to add bases suitable for catching the liberated hydrogen chloride, for example sodium hydroxide, sodium carbonate, sodium bicarbonate, sodium acetate, trisodium phosphate, disodium phosphate or monosodium phosphate, sodium formate, sodium propionate. The preferred solvent in these condensation reactions for economic reasons is water, in order to avoid the regeneration of organic solvents.

However, it is possible for the reaction medium to contain solvents which are miscible with water, for example alcohols, such as methanol, ethanol or isopropanol or solvents which are not miscible with water, for example methylene chloride, chloroform, carbon tetrachloride, dichloroethane, trichloroethane, n-hexane, cyclohexane, toluene, xylene, monochlorobenzene, o-dichlorobenzene.

Furthermore, it is possible to add to the reaction medium used in the condensation reactions known surface active agents, for example anionic surface active agents, cationic surface active agents, amphoteric surface active agents or non-ionogenic surface active agents (cf. Ullmanns Enzyclopädie der technischen Chemie, volume 16, pages 724–748 (1965) or "Surface Activity" by J. L. Moilliet, B. Collie and Black, 2nd edition, chapters 10–15). The addition of surface active agents increases the reaction speed of the condensation reactions. The condensation reactions have normally ended after reaction periods of 1 to 6 hours at 0° to 50° C.

The condensation products of formula (IV) occur as compounds which are sparingly soluble in water in yields of 80 to 100% of the theoretical yield and can then be converted, preferably without further purification and intermediate isolation, into the heterocyclic diamines of formula I by reduction and cyclization.

According to a specially preferred form of embodiment of the present invention, the reaction stages of reduction and cyclization are combined into a single stage.

According to this preferred variant (a) of the process, the condensation products of the formula (IV) are reduced with sulfide reducing agents, such as for example hydrogen sulfide, alkali sulfides or alkali polysulfides, especially with an alkali hydrogen sulfide, for example the technically usual sulfhydrate liquor (sodium hydrogen sulfide).

In these reduction processes the intermediate products of formula IV are surprisingly converted direct into the heterocyclic diamines of the formula (I) at pH values of between 8 and 14, preferably 9 and 13, and at temperatures of 50° to 150° C., preferably 80° to 130° C. The end products of the formula (I) are then isolated from the aqueous reaction medium in high yields and of excellent quality.

Another variant (b) of the process for converting the condensation products of formula IV into the heterocyclic diamines of formula I consists in first of all reducing the 3- or 4-nitrobenzoic acid-2'-amino-5'-nitroanilides (IV) with the quantity of a sulfide reducing agent, such as hydrogen sulfide, alkali sulfide, alkali polysulfide or alkali hydrogen sulfide, preferably sodium hydrogen sulfide, necessary for the reduction of one nitro group, selectively at pH values of 8 to 14, preferably 9 to 13, at temperatures of 50° to 150° C., preferably 80° to 130° C., to form the 3- or 4-aminobenzoic acid-2'-amino-5'-nitroanilides of formula VII, and these are then cyclised at alkaline pH values of 8 to 14, preferably 9 to 13, and at temperatures of 50° to 150° C., preferably 80° to 130° C., to give the 2-(3'- or 4'-aminophenyl)-5(or 6)-nitrobenzimidazoles of formula VIII.

These intermediate products are then further reduced, also in an alkaline pH range of 8 to 14, preferably 9 to 13, and at temperatures of 50° to 150° C., preferably 80° to 130° C., with the above-mentioned sulfide reducing agents, preferably sodium hydrogen sulfide, to give the heterocyclic diamines of formula (I).

Also according to this variant of the process it is possible for the condensation products of formula IV to be converted into the end products of formula (I) without the isolation of intermediate stages and using a so-called single-vessel process. In this case the heterocyclic diamines of formula (I) also occur in excellent quality and in high yields, which is surprising in view of the fact that the process operates over several stages without intermediate isolation and purification of the intermediates which occur.

A further variant (c) of the process consists in, first of all, converting the condensation products of the formula (IV) obtained from 4-nitro-1,2-diaminobenzenes of formula (II) and 3- or 4-nitrobenzoic acid chlorides of formula (III) by cyclization at alkaline pH values of 8 to 14, preferably 10 to 13, and at temperatures of 50° to 150° C., preferably 80° to 130° C., into the 2-(3'- or 4'-nitrophenyl)-5(or 6)-nitrobenzimidazoles (IX), which then, preferably without intermediate isolation and purification, are reduced in an alkaline aqueous reaction medium at a pH of 8 to 14, preferably 9 to 13, and at temperatures of 50° to 150° C., preferably 80° to 130° C., by reduction with sulfide reducing agents, such as hydrogen sulfide, alkali sulfides, alkali polysulfides or alkali hydrogen sulfide, preferably sodium hydrogen sulfide, to the heterocyclic diamines of formula (I).

Also according to variant (c) of the process the reduction of the two nitro groups is carried out in stages via 2-(3'- or 4'-aminophenyl)-5(or 6)-nitrobenzimidazoles of formula VIII, although their intermediate isolation and purification is not necessary for the production of the end products (I).

According to this variant of the process, the diamines of formula (I) can also be isolated in high yields and in excellent quality which is surprising in view of the multi-stage reaction and was not to be foreseen.

The 2-[3'- or 4'-aminophenyl]-5(or 6)-aminobenzimidazoles of the general formula (I) produced according to the process of the invention can be isolated both in the form of the free bases and also in the form of their salts of organic or inorganic acids, preferably their salts of hydrochloric acid or sulfuric acid, that is to say as hydrochlorides or hydrogen sulfates. In the form of the free bases as well as their hydrochlorides or hydrogen sulfates they are valuable intermediates for the production of dyestuffs, optical brighteners, temperature-resistant polymers, for example polyamides, and also plant protection products. The preparation of dyestuffs with 2-[3'- or 4'-aminophenyl]-5(or 6)-aminobenzimidazole as starting material is described, for instance, in U.S. Pat. No. 4,033,945.

As initial material for the production of dyestuffs those diamines of formula I are preferred in which $R_1$ and/or $R_2$ signify hydrogen, methyl, methoxy or chlorine.

As 4-nitro-1,2-diaminobenzenes of general formula (II) it is possible for example to use in the process of the present invention: 4-nitro-1,2-diaminobenzene, 4-nitro-5-methyl-1,2-diaminobenzene, 4-nitro-6-methyl-1,2-diaminobenzene, 4-nitro-6-methoxy-1,2-diaminobenzene, 4-nitro-6-chloro-1,2-diaminobenzene, 4-nitro-6-bromo-1,2-diaminobenzene, 4-nitro-5-ethyl-1,2-diaminobenzene, 4-nitro-5-n-butyl-1,2-diaminobenzene, 4-nitro-6-ethoxy-1,2-diaminobenzene, 4-nitro-6-n-butoxy-1,2-diaminobenzene.

With regard of the use of the diamines of formula I produced according to the invention for the production of azo dyestuffs, the use of 4-nitro-1,2-diaminobenzenes of the general formula II in which $R_1$ signifies hydrogen, methyl, methoxy or chlorine, is specially preferred.

The use of substituted 4-nitro-1,2-diaminobenzenes of formula (II) for example of the type mentioned, permits of the introduction of substituents $R_1$ into the heterocyclic diamines of formula (I).

The 4-nitro-1,2-diaminobenzenes of formula (II) are accessible from the 2,4-dinitroanilines by reduction processes known from the literature, for example by reduction with hydrogen sulfide, sulfides and polysulfides (cf. for example Houben-Weyl, Methoden der Organischen Chemie, vol. XI/1, pages 409–421 (1957), Organic Syntheses, vol. 21, page 20 (1941), or by selective catalytic hydrogenation (cf. for example R. E. Lyle and J. L. La Mattina, Synthesis 1974, 726).

As 3- or 4-nitrobenzoic acids of formula (VI) which are suitable for the production of the 3- or 4-nitrobenzoic acid chlorides (III) necessary for the condensation reaction with the 4-nitro-1,2-diaminobenzenes of formula (II) (cf. reaction diagram 1), it is possible to use for example: 4-nitrobenzoic acid, 2-methyl-4-nitrobenzoic acid, 3-methyl-4-nitrobenzoic acid, 3,5-dimethyl-4-nitrobenzoic acid, 2-ethyl-4-nitrobenzoic acid, 2-methoxy-4-nitrobenzoic acid, 3-methoxy-4-nitrobenzoic acid, 2,3-dimethoxy-4-nitrobenzoic acid, 3,5-dimethoxy-4-nitrobenzoic acid, 2-methyl-5-methoxy-4-nitrobenzoic acid, 3-ethoxy-4-nitrobenzoic acid, 3-methyl-6-methoxy-4-nitrobenzoic acid, 2-chloro-4-nitrobenzoic acid, 3-chloro-4-nitrobenzoic acid, 2-bromo-4-nitrobenzoic acid, 3-bromo-4-nitrobenzoic acid, 3-nitrobenzoic acid, 2-methyl-3-nitrobenzoic acid, 4-methyl-3-nitrobenzoic acid, 5-methyl-3-nitrobenzoic acid, 6-methyl-3-nitrobenzoic acid, 6-ethyl-3-nitrobenzoic acid, 2,4-dimethyl-3-nitrobenzoic acid, 4,6-dimethyl-3-nitrobenzoic acid, 2-methoxy-3-nitrobenzoic acid, 4-methoxy-3-nitrobenzoic acid, 6-methoxy-3-nitrobenzoic acid, 4-ethoxy-3-nitrobenzoic acid, 5-methyl-6-methoxy-3-nitrobenzoic acid, 4-methoxy-5-methyl-3-nitrobenzoic acid, 4-methyl-6-methoxy-3-nitrobenzoic acid, 5,6-dimethoxy-3-nitrobenzoic acid, 2,4-dimethoxy-3-nitrobenzoic acid, 2,5-dimethoxy-3-nitrobenzoic acid, 4,5-dimethoxy-3-nitrobenzoic acid, 2-chloro-3-nitrobenzoic acid, 4-chloro-3-nitrobenzoic acid, 5-chloro-3-nitrobenzoic acid, 6-chloro-3-nitrobenzoic acid, 2,5-dichloro-3-nitrobenzoic acid, 2,6-dichloro-3-nitrobenzoic acid, 4,6-dichloro-3-nitrobenzoic acid, 2-bromo-3-nitrobenzoic acid, 4-bromo-3-nitrobenzoic acid, 5-bromo-3-nitrobenzoic acid, 6-bromo-3-nitrobenzoic acid, 4,5-dibromo-3-nitrobenzoic acid, 3-ethyl-4-nitrobenzoic acid, 3-n-butyl-4-nitrobenzoic acid, 3-ethoxy-4-nitrobenzoic acid, 3-n-butoxy-4-nitrobenzoic acid.

The production according to the invention of diamines of the formula I which are to be used as initial material for dyestuff productions, one preferably uses those 3- or 4-nitrobenzoic acid derivatives of formula VI in which $R_2$ is hydrogen, methyl, methoxy or chlorine.

By using substituted 3- or 4-nitrobenzoic acids, for example of the type mentioned, it is possible to introduce substituents $R_2$ into the heterocyclic diamines (I).

The examples which follow will serve to illustrate the process according to the present invention. The parts signify parts by weight, the temperatures are given in degrees centigrade.

EXAMPLE 1

A mixture of 184 parts of 4-nitrobenzoic acid, 260 parts of toluene and 167 parts of thionyl chloride are mixed with 3 parts of dimethylformamide and heated to 80° C. within 7 hours accompanied by agitation. The gases—hydrogen chloride and sulfur dioxide—which are liberated in this way are absorbed in two stages in 200 parts of water and then in 400 parts of 20% sodium hydroxide solution.

Obtained is a clear solution of 4-nitrobenzoyl chloride in toluene, which, after cooling to about 20° to 25° C., is added to a mixture of 153.2 parts of 4-nitro-1,2-diaminobenzene and 500 parts of ice in 1500 parts of water. Stirring is continued for a further 3 hours at 5° to 10° C., the yellow suspension of the resultant 4-nitrobenzoic acid-2'-amino-5'-nitroanilide which results (348°–350° C.) is heated to 50° C. and it is adjusted to a pH of 7–7.5 with a solution of 56 parts of sodium hydroxide in 150 parts of water.

Then at 50° to 60° C. there are run in 725 g of a 32% aqueous sulfhydrate liquor (sodium hydrogen sulfide). After this, the reaction mixture is heated to 95° to 100° C., when the toluene employed is recovered by destillation. After a reaction time of 10 to 12 hours at 95° to 100° C. it is cooled to 5° to 10° C.; the product is isolated by filtration, washed with water and dried at 70° to 80° C.

Obtained are 206 parts of 2-(4'-aminophenyl)-5(or 6)-aminobenzimidazole (M.P.: 140°–142° C.) with a purity of 91%.

The filtrate of the sulfhydrate reduction is adjusted to a pH of 7 with the sodium bisulphite solution obtained in the 4-nitrobenzoic acid chloride production. Then about 200 parts of the approximately 20% hydrochloric acid obtained by absorption are added. Then it is stirred for a further 1 to 2 hours, the precipitated sulfur is filtered off, thus obtaining a filtrate which contains sodium chloride and sodium sulfate and is free from low-valent sulfur compounds.

EXAMPLE 2

The condensation of 153.2 parts of 4-nitro-1,2-diaminobenzene with 204 parts of 4-nitrobenzoyl chloride is carried out in accordance with the instructions of Example 1. The suspension of the 4-nitrobenzoic acid-2'-amino-5'-nitroanilide is heated to 50° C. and is neutralised with a solution of 56 parts of sodium hydroxide in 150 parts of water.

Then one adds, at 50° C., 360 g. of 32% aqueous sulfhydrate liquor and the temperature of the reaction mixture is raised to 95° to 100° C., when the toluene used is recovered by distillation. The yellow suspension of the reduction product 4-amino-benzoic acid-2'-amino-5'-nitroanilide (237°–239° C.) is then mixed at 95° C. with a solution of 20 parts of sodium hydroxide in 50 parts of water, and it is stirred for 1 hour at 95° C. and a pH of 10.5 to 12, when cyclization occurs to give 2-(4'-aminophenyl)-5-(or 6)-nitrobenzimidazole (285°–290° C.). The suspension of the cyclization product is cooled to approximately 90° C. and is mixed with 363 g. of a 32% sulfhydrate liquor. In order to complete the reduction it is stirred for 10 to 12 hours at 95° to 100° C., then cooled to 5° to 10° C., filtered and washed again with water. After drying at approximately 70° to 80° C., one obtains 207 g. of 2-(4'-aminophenyl)-5(or 6)-aminobenzimidazole (M.P. 140°–142° C.) with a purity of 92%.

EXAMPLE 3

The condensation of 153.2 parts of 4-nitro-1,2-diaminobenzene with 204 parts of 4-nitrobenzoyl chloride is carried out in accordance with the instructions of Example 1. The yellow suspension of the condensation product 4-nitrobenzoic acid-2'-amino-5'-nitroanilide is heated to 50° C. and adjusted to a pH of 10.5 to 12 with a solution of 96 g of sodium hydroxide in 250 parts of water. When the temperature is raised to 95° to 100° C., the toluene employed is recovered by distillation. The cyclization to 2-(4'-nitrophenyl)-5-(or 6)-nitrobenzimidazole (350°–353° C.) is terminated after stirring for about 1 hour at 95° to 100° C. The yellow suspension of the cyclization product is then cooled to about 80° C. and then mixed with 725 g of a 31.7% aqueous sulfhydrate liquor. The reaction mixture is stirred for 10 to 12 hours at 95° to 100° C. and then cooled to 5° to 10° C. The product is isolated by filtration and washed with water. Obtained are 205 g. of 2-(4'-aminophenyl)-5(or 6)-aminobenzimidazole (140°–142° C.) with a purity of 91%.

The following table shows further examples of 2-(3'- or 4'-aminophenyl)-5(or 6)-aminobenzimidazoles of formula (I) which can be produced according to the above Examples from the 3- or 4-nitrobenzoic acid-2'-amino-5'-nitroanilides of formula (IV) obtained by the condensation of 4-nitro-1,2-diaminobenzenes of formula (II) and 3- or 4-nitrobenzoic acid chlorides of formula (III).

The table gives the following information:

In column 1: the 4-nitro-1,2-diaminobenzene of formula (II) used

In column 2: the 3- or 4-nitrobenzoic acid chloride of formula (I) used

In column 3: the structure of the 2-(3'- or 4'-aminophenyl)-5(or 6)-aminobenzimidazole of formula (I) obtained In column 4: the yield of (I) as a percentage of the theoretical yield, reckoned on the 4-nitro-1,2-diaminobenzene (II) employed.

| Initial Products of | | | % of |
|---|---|---|---|
| Formula (II) | Formula (III) | End product of formula (I) | Theory |
| 4-nitro-1,2-diaminobenzene | 3-nitrobenzoyl chloride | 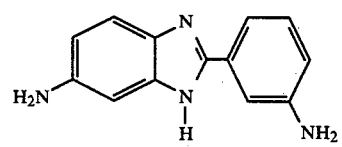 | 77 |

-continued

| Initial Products of | | End product of formula (I) | % of Theory |
|---|---|---|---|
| Formula (II) | Formula (III) | | |
| 4-nitro-1,2-diaminobenzene | 2-methyl-4-nitrobenzoyl chloride | benzimidazole with H₂N-, -NH₂, -CH₃ substituents | 79 |
| 4-nitro-1,2-diaminobenzene | 3-methyl-4-nitrobenzoyl chloride | benzimidazole with H₂N-, -NH₂, -CH₃ substituents | 81 |
| 4-nitro-1,2-diaminobenzene | 2-chloro-4-nitrobenzoyl chloride | benzimidazole with H₂N-, -NH₂, -Cl substituents | 69 |
| 4-nitro-1,2-diaminobenzene | 3-chloro-4-nitrobenzoyl chloride | benzimidazole with H₂N-, -NH₂, -Cl substituents | 80 |
| 4-nitro-1,2-diaminobenzene | 3-methoxy-4-nitrobenzoyl chloride | benzimidazole with H₂N-, -NH₂, -OCH₃ substituents | 81 |
| 4-nitro-1,2-diaminobenzene | 3-nitro-4-methoxy-benzoyl chloride | benzimidazole with H₂N-, -OCH₃, -NH₂ substituents | 79 |
| 4-nitro-1,2-diaminobenzene | 3-nitro-4-methyl-benzoyl chloride | benzimidazole with H₂N-, -CH₃, -NH₂ substituents | 76 |
| 4-nitro-6-chloro-1,2-diaminobenzene | 4-nitrobenzoyl chloride | benzimidazole with Cl, H₂N-, -NH₂ substituents | 82 |
| 4-nitro-5-methyl-1,2-diaminobenzene | 4-nitrobenzoyl chloride | benzimidazole with H₃C-, H₂N-, -NH₂ substituents | 81 |
| 4-nitro-6-methyl-1,2-diaminobenzene | 4-nitrobenzoyl chloride | benzimidazole with CH₃, H₂N-, -NH₂ substituents | 80 |
| 4-nitro-6-chloro-1,2-diaminobenzene | 2-chloro-4-nitrobenzoyl chloride | benzimidazole with Cl, H₂N-, -NH₂, Cl substituents | 75 |

-continued

| Initial Products of | | End product of formula (I) | % of Theory |
|---|---|---|---|
| Formula (II) | Formula (III) | | |
| 4-nitro-6-chloro-1,2-diaminobenzene | 3-chloro-4-nitrobenzoyl chloride | 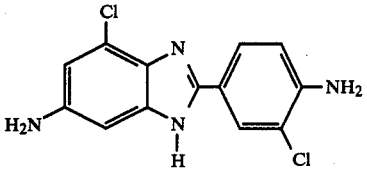 | 81 |

We claim:

1. In the process for the production of compounds of the formula

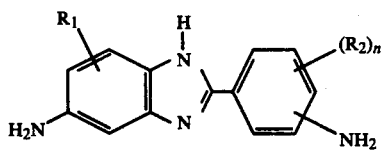

wherein $R_1$ and $R_2$ are the same or different and each is hydrogen, alkyl having 1 to 4 carbon atoms, alkoxy having 1 to 4 carbon atoms, chlorine or bromine, and n is 1 or 2, comprising reacting a compound of the formula

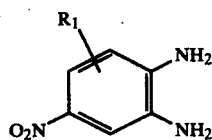

with a compound of the formula

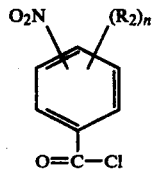

to form the anilide of the formula

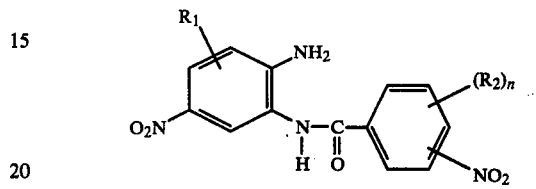

and cyclizing and reducing said anilide wherein the improvement comprises cyclizing the anilide in an aqueous alkaline medium and reducing the nitro moieties with a sulfide reductant.

2. The process of claim 1 wherein the reduction and recylization is effected at a pH of 8 to 14.

3. The process of claim 1 wherein the reduction and cyclization is effected at a pH of 9 to 13.

4. The process of claim 1 wherein the reduction and cyclization is carried out at temperatures of between 50° and 150° C.

5. The process of claim 1 wherein the reduction and cyclization is carried out at temperatures of between 80° and 130° C.

6. The process of claim 1 wherein a nitro group of the anilide is reduced selectively to a compound of the formula

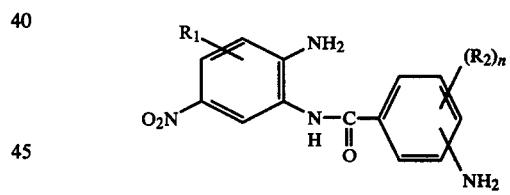

which is then cyclized and reduced.

7. The process of claim 1 wherein the cyclization and reduction of the anilide is effected simultaneously without isolating the intermediates.

8. The process of claim 1 wherein the anilide is produced in a reaction environment containing water or an organic solvent miscible with water at a pH of 1 to 10 and at temperatures of between −10° and 100° C.

9. The process of claim 1 wherein the anilide is cyclized and after cyclization the nitros are reduced.

* * * * *